United States Patent [19]

Carr

[11] 4,308,276

[45] Dec. 29, 1981

[54] INHIBITING LIPOGENESIS WITH BENZOXATHIINCARBOXAMIDES

[75] Inventor: John B. Carr, Houston, Tex.

[73] Assignee: Shell Oil Company, Houston, Tex.

[21] Appl. No.: 937,032

[22] Filed: Aug. 25, 1978

Related U.S. Application Data

[63] Continuation-in-part of Ser. No. 811,646, Jun. 30, 1977, abandoned.

[51] Int. Cl.$^3$ .............................................. A61K 31/39
[52] U.S. Cl. ...................................... 424/276; 549/15; 564/305
[58] Field of Search ........................ 260/327 P, 340.3; 424/276; 549/15

[56] References Cited

U.S. PATENT DOCUMENTS

| | | | |
|---|---|---|---|
| 3,117,978 | 1/1964 | Biel et al. | 260/340.3 |
| 3,496,183 | 2/1970 | Toldy et al. | 260/268 |
| 4,118,507 | 10/1978 | Carr | 260/340.3 X |

OTHER PUBLICATIONS

Fischer et al., Chem. Absts., vol. 84, Abst. No. 84: 44208n (1976) (Abst. of Hung. Telies 10,009, pub. 6-2-8-75).
Fourneau et al., Arch. Intern. Pharm., vol. 46, p. 178 (1933).
Goldenberg et al., J. Am. Med. Assoc., vol. 135, p. 971 (1947).
Koo et al., J. Am. Chem. Soc., vol. 77, pp. 5373-5375 (1955).
Martin et al., J. Org. Chem., vol. 39, pp. 1811-1814 (1974).
Tsai et al., J. Pharm. Sci., vol. 61, pp. 228-231 (1972).

*Primary Examiner*—Richard A. Schwartz

[57] ABSTRACT

2,3-Dihydro-N-(2-propenyl)-1,4-benzoxathiin-2-carboxamides, useful as lipogenesis inhibitors in mammals.

1 Claim, No Drawings

INHIBITING LIPOGENESIS WITH BENZOXATHIINCARBOXAMIDES

This application is a continuation-in-part of application Ser. No. 811,646, filed on June 30, 1977, now abandoned.

DESCRIPTION OF THE INVENTION

It has been found that lipogenesis in mammals is inhibited by 2,3-dihydro-N-(2-propenyl)-1,4-benzoxathiin-2-carboxamides, which can be described by the formula:

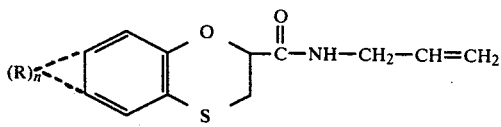

wherein n is zero or one, R is halogen, nitro, amino, methylsulfonylamino, trifluoromethyl, alkyl or alkoxy of from one to six carbon atoms or phenyl. By halogen is meant chlorine, fluorine, bromine and iodine, the middle halogens, bromine and chlorine, being preferred. Each alkyl moiety may be of straight-chain or branched-chain configuration.

In formula I, the dotted lines from the moiety R to the carbon atoms of the ring structure indicate that the contemplated compounds include those wherein the moiety R is bonded to the ring at the 6-position or at the 7-position of the ring.

For illustration, preparation of typical individual species of the genus defined by Formula I are described in the examples included hereinafter. Other typical, illustrative individual species are those wherein

| n = 1; R = | n = 1; R = |
|---|---|
| 6-fluoro, | 6-phenyl |
| 7-nitro | 7-methoxy |
| 7-amino | 7-trifluoromethyl |
| 7-methyl-sulfonylamino | 7-chloro |

Compounds of Formula I can be prepared by heating an alkyl, suitably methyl or ethyl, ester of the corresponding carboxylic acid, in solution in a suitable solvent such as ethanol, with 2-propenamine. Suitably, the reaction can be effected by refluxing the mixture. Preferably, about a four-to-six-fold excess of the amine is used. The desired product can be recovered by evaporating the solvent and excess amine, then employing conventional techniques, such as selective extraction, recrystallization and/or dry-column chromatography, to isolate the desired product. Use of these procedures and techniques in particular instances is illustrated in the working examples included hereinafter.

Alternatively, the amides can be prepared by treating the corresponding carboxylic acid with thionyl chloride, to form the corresponding acid chloride, then treating the acid chloride with the amine. An excess of the thionyl chloride is used, in part acting as solvent. Conveniently, the treatment is conducted by refluxing the mixture. The excess thionyl chloride then is evaporated and the acid chloride can be isolated. Alternatively, the crude product can be treated with an excess of the amine, a solvent such as methylene chloride being added if needed to moderate the reaction and/or to ensure a liquid reaction mixture. The desired product can be recovered from the reaction mixture as indicated above.

The precursor esters can be prepared by condensing methyl or ethyl 2,3-dibromopropionate with the appropriate R-2-mercaptophenol in the presence of a base such as potassium carbonate, and in a solvent such as acetone at or somewhat above room temperature.

The precursor mercaptophenols can be prepared by (a) diazotizing the appropriate R-2-aminophenol, (b) treating potassium ethylxanthate with the resulting diazonium salt, and (c) reducing the resulting xanthate with lithium aluminum hydride, each of these steps being conducted according to the method described at page 570, Djerassi et al., J. Am. Chem. Soc., 77, 568–571 (1955).

Some of the precursor aminophenols (R=H, chlorine, methyl, methoxy, nitro) are known. 2-Amino-4-(trifluoromethyl)phenol has been prepared as follows.

87.6 g of finely powdered sodium hydroxide was added in portions over an 8-hour period to a stirred solution of 164.0 g of 2-nitro-4-(trifluoromethyl)chlorobenzene in 220 ml of dimethyl sulfoxide at room temperature. The mixture was acidified to pH 1 with concentrated hydrochloric acid. An oil formed; it was separated and dissolved in ether. The solution was dried (MgSO$_4$) and stripped of solvent under reduced pressure. The residue was mixed with cold sodium hydroxide solution. The mixture was extracted with petroleum ether. The water layer was acidified with concentrated hydrochloric acid. An oil that formed was separated and dissolved in ether. The solution was dried (MgSO$_4$) and stripped of solvent to give 2-nitro-4-(trifluoromethyl)phenol (A).

82.2 g of A was dissolved in 300 ml of ethanol. 0.5 g of platinum oxide catalyst was added and the mixture was hydrogenated at 50 psig. The resulting solution was filtered, and the filtrate was concentrated. The residue was crystallized from water to give 2-amino-4-(trifluoromethyl)phenol.

Those species wherein R is amino can be prepared as shown in Example 6.

The species wherein R is methylsulfonylamino can be prepared as shown in Example 7.

The procedures for preparing compounds of Formula I are illustrated in the following examples. In each case, the identities of the product, and of the precursor(s) involved, were confirmed by appropriate chemical and spectral analyses.

Example 1—2,3-Dihydro-N-(2-propenyl)-1,4-benzoxathiin-2-carboxamide (1)

To a stirred mixture of 41.6 g of ethyl 2,3-dibromopropionate, 400 ml of dry acetone and 11.1 g of potassium carbonate, there was added dropwise at 27° C. a solution of 19.5 g of o-mercaptophenol in 75 ml of acetone. After the addition was complete, the reaction mixture was stirred at room temperature for 10 minutes and an additional 50.9 g of potassium carbonate was added. The reaction mixture then was refluxed for 2 hours, and allowed to stand overnight at room temperature. The mixture was filtered and the solid was washed with acetone, the washings being added to the filtrate. The acetone was stripped to leave a liquid, which was taken up in methylene chloride. The resulting solution was washed with water and dried (MgSO$_4$), and the solvent was stripped. The resulting liquid was dry column chromatographed through silica gel, using a 4:16:80 by volume mixture of tetrahydrofuran, ethyl acetate and hexane (Solvent No. 2) as eluent, to give the ethyl ester of 2,3-dihydro-1,4-benzoxathiin-2-carboxylic acid (1A), as a light yellow liquid, boiling point not determined.

A solution of 4.5 g of 1A and 3.4 g of 2-propenamine in 25 ml of ethanol was refluxed for 20 hours. The solvent and excess amine then were stripped off and the residue was dry column chromatographed over silica gel, using Solvent No. 2 as eluent, to give, (after extraction and removal of solvent), 1, as a viscous yellow liquid, boiling point not determined.

Example 2—2,3-Dihydro-6-methyl-N-(2-propenyl)-1,4-benzoxathiin-2-carboxamide (2)

A solution of 20.0 g of 4-methyl-2-mercaptophenol in 75 ml of acetone was added slowly to a stirred mixture of 40.2 g of ethyl 2,3-dibromopropionate and 10.2 g of potassium carbonate in 400 ml of acetone, at room temperature. The mixture was stirred at room temperature for 10 minutes, then refluxed for 16 hours. The mixture was filtered and the solid was washed with acetone. The acetone filtrate was stripped of solvent; the residue was dissolved in methylene chloride, the solution was washed with water, then dried (MgSO$_4$) and stripped of solvent. The liquid residue was dry column chromatographed (silica gel) using Solvent No. 2 as eluent. The first band (high Rf) was collected and extracted with ether. The solvent was stripped from the extract. The residue was dried (vacuum, 24 hours) and crystallized from hexane to give the ethyl ester of 2,3-dihydro-6-methyl-1,4-benzoxathiin-2-carboxylic acid (2A), as white needles, mp: 41°–43° C.

A mixture of 10.4 g of 2A, 15 g of 2-propenamine in 20 ml of ethanol was stirred for 24 hours at room temperature. The solvent was stripped under vacuum. The residue was recrystallized from hexane to give 2, as a solid, mp: 86°–88° C.

Example 3—6-Chloro-2,3-dihydro-N-(2-propenyl)-1,4-benzoxathiin-2-carboxamide (3)

By the procedures described in Examples 1 and 2, the ethyl ester of 6-chloro-2,3-dihydro-1,4-benzoxathiin-2-carboxylic acid (3A) was prepared as a solid, mp: 64°–66° C., from 4-chloro-2-mercaptophenol.

3A was treated with 2-propenamine according to the procedures described in Examples 1 and 2, to give 3, as a solid, mp: 98°–100° C.

Example 4—6-(Trifluoromethyl)-2,3-dihydro-N-(2-propenyl)-1,4-benzoxathiin-2-carboxamide (4)

4 was prepared (as white crystals, mp: 99°–101° C.) from 2-amino-4-(trifluoromethyl)phenol, by the procedures described herein.

Example 5—6-Nitro-2,3-dihydro-N-(2-propenyl)-1,4-benzoxathiin-2-carboxamide (5)

5 was prepared (as pale yellow crystals, mp: 142°–144° C.) from 4-nitro-2-mercaptophenol by the procedures described in Examples 1–3.

Example 6—6-Amino-2,3-dihydro-N-(2-propenyl)-1,4-benzoxathiin-2-carboxamide (6)

6 was prepared by adding 71 ml of concentrated ammonium hydroxide to a mixture of 33.0 g of 5, 250 ml of water, 250 ml of methanol and 250 ml of methylene chloride, at room temperature, adding 123.0 g of sodium dithionite over a period of 40 minutes, in portions, to the stirred mixture at room temperature, heating the mixture to 34°–37° C. and holding it at this temperature for 2 hours. Then 1000 ml of methylene chloride was added, the methylene chloride phase was separated, dried (MgSO$_4$), the solvent evaporated under vacuum and the resulting solid recrystallized from a 50/50 by volume mixture of methylene chloride and hexane to give 6, as tan-colored crystals, mp; 106°–108° C.

Example 7—6-Methylsulfonamido-3,4-dihydro-N-(2-propenyl)-1,4-benzoxathiin-2-carboxamide (7)

7 was prepared by adding 1.98 g of methanesulfonyl chloride drop-by-drop to a mixture of 3.9 g of 6 and 1.75 g of triethylamine, at 0°–5° C., then heating it to room temperature and stirring it at that temperature for 2 hours. The mixture was filtered, the filtrate was washed with water, dried (MgSO$_4$), the solvent was evaporated, the residue was washed with 20 ml of methylene chloride, then with 30 ml of ether, to give a yellow solid, which on recrystallization from a 40:100 by volume mixture of ethanol and chloroform gave 7, mp: 200°–202° C.

Example 8—2,3-Dihydro-7-methyl-N-(2-propenyl)-1,4-benzoxathiin-2-carboxamide (8)

8 was prepared (as a solid, mp 50° C.) from 2-amino-5-methylphenol by the procedures described in Examples 1–3, the precursor mercaptophenol having been prepared according to the method described in Djerassi, et al., supra.

Example 9—2,3-Dihydro-6-methoxy-N-(2-propenyl)-1,4-benzoxathiin-2-carboxamide (9)

4-Methoxy-2-nitrophenol (9A) was prepared by treating 2-nitro-4-methoxyaniline with arsenic trioxide and sodium hydroxide in water.

4-Methoxy-2-aminophenol (9B) was prepared by treating a mixture of 9A and ammonium hydroxide in water with sodium dithionite. 9B was converted to 4-methoxy-2-mercaptophenol (9C) according to the methods described in Djerassi, et al. 9C was converted to 9 (a solid, mp 73°–75° C.) by the procedures described in Examples 1–3.

The carboxamides of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the up-take of the radioactive carbon by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure.

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-U$^{14}$C, and 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound in each case. The data obtained from the tests are set out in Table 1, as the percent inhibition of lipogenesis compared to the results obtained in the control tests wherein only the test compound was omitted.

TABLE I

| Compound No. | Percent Inhibition |
|---|---|
| 1 | 63 |
| 2 | 63 |
| 3 | 54 |
| 4 | 30 |
| 5 | 45 |
| 6 | 29 |
| 7 | 46 |
| 8 | 26 |

The carboxamides of Formula I can be used to control lipogenesis in warm-blooded animals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the carboxamides orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboxamide used, and the particular animal being treated. However, in general, satisfactory results are obtained when the carboxamides are administered in a dosage of from about 1 to about 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used as the inhibitor, and the professional judgment of the person administering or supervising the administration of the inhibitor. It is to be understood that the dosages set forth herein are exemplary only, and that they do not, to any extent, limit the scope or practice of the invention.

What is claimed is:

1. A method of inhibiting lipogenesis in a mammal, which comprises administering, to a mammal in need of such treatment, orally or parenterally, an effective amount of a compound of the formula

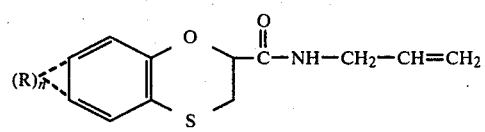

wherein n is zero or one, R is halogen, nitro, amino, methylsulfonylamino, trifluoromethyl, alkyl or alkoxy of from one to six carbon atoms, or phenyl.

* * * * *